United States Patent
Bevis

(10) Patent No.: US 7,940,386 B1
(45) Date of Patent: May 10, 2011

(54) SCATTEROMETRY TARGET EMPLOYING NON-PERIODIC DEFECT FEATURES TO ENHANCE OR OPTIMIZE TARGET SENSITIVITY TO A PARAMETER OF INTEREST

(75) Inventor: Christopher F. Bevis, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 771 days.

(21) Appl. No.: 11/848,158

(22) Filed: Aug. 30, 2007

Related U.S. Application Data

(60) Provisional application No. 60/949,801, filed on Jul. 13, 2007.

(51) Int. Cl.
*G01J 1/10* (2006.01)
(52) U.S. Cl. .................................................. 356/243.4
(58) Field of Classification Search .................. None
See application file for complete search history.

(56) References Cited

U.S. PATENT DOCUMENTS

| | | | | |
|---|---|---|---|---|
| 4,386,850 | A * | 6/1983 | Leahy | 356/243.4 |
| 5,004,340 | A * | 4/1991 | Tullis et al. | 356/243.6 |
| 6,274,396 | B1 * | 8/2001 | Funsten | 356/243.4 |
| 7,538,867 | B2 * | 5/2009 | Murai | 356/237.5 |
| 2004/0264903 | A1 * | 12/2004 | Dridi et al. | 385/129 |
| 2008/0131660 | A1 * | 6/2008 | Noda et al. | 428/138 |

* cited by examiner

*Primary Examiner* — Gregory J Toatley
*Assistant Examiner* — Juan D Valentin
(74) *Attorney, Agent, or Firm* — Suiter Swantz pc llo

(57) ABSTRACT

Embodiments of the invention include a target having a lattice of many periodically spaced and uniformly configured metrology features arranged in an array pattern over a target region. The lattice includes at least one defect region in the lattice, the defect region includes at least one intentionally introduced defect metrology feature. The defect feature configured to enable increased sensitivity of the target to a selected parameter of interest. The invention further encompassing associated methods of implementing the target and evaluating the parameter of interest.

18 Claims, 7 Drawing Sheets

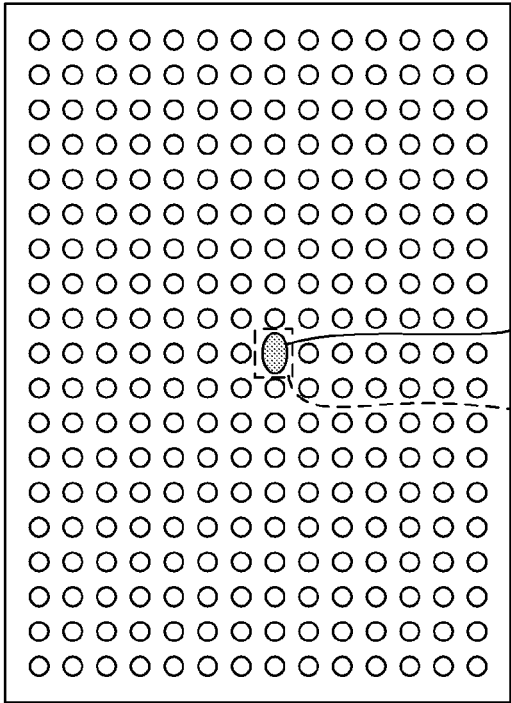
Fig. 3(e)
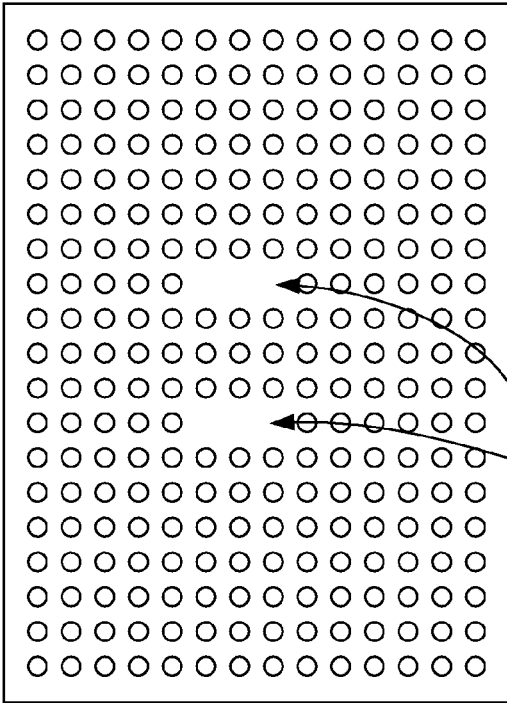
Fig. 3(f)
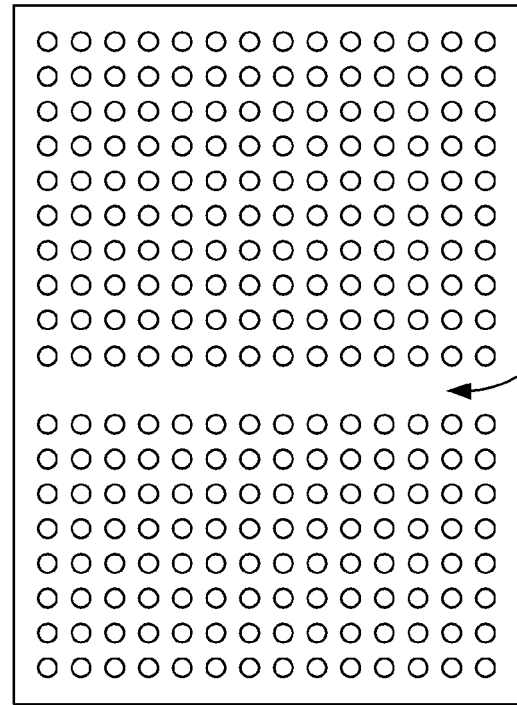
Fig. 3(g)
Fig. 3(h)

SCATTEROMETRY TARGET EMPLOYING NON-PERIODIC DEFECT FEATURES TO ENHANCE OR OPTIMIZE TARGET SENSITIVITY TO A PARAMETER OF INTEREST

This application claims priority to U.S. Provisional Application No. 60/949,801 filed Jul. 13, 2007, entitled "Scatterometry Target Employing Non-Periodic Features to Enhance or Optimize Target Sensitivity to a Parameter of Interest" by Christopher F. Bevis which application is hereby incorporated by reference.

TECHNICAL FIELD

The invention described herein relates generally to scatterometry targets having a high degree of sensitivity to parameters of interest and methodologies for generating such targets. Particularly, the invention refers to target embodiments wherein a patterned target array includes an intentionally introduced defect that enables measurements of the target to have increased sensitivity to a parameter of interest that is related to the defect.

BACKGROUND

As is well-understood in the art, periodic scatterometry targets are used to obtain accurate measurements of target features. Such targets include massive arrays of uniformly constructed and uniformly spaced periodic features arranged to provide the best possible sensitivity to the measured parameters. Typical prior art example targets include periodic gratings or periodically configured higher dimensional target arrays comprised of a plurality of uniformly spaced and sized metrology features.

In either case such targets have a finite degree of sensitivity. In one typical example, a scatterometry target can be used to, for example, measure a target array (for example and array of 100 nm diameter "dots" or features). Such a scatterometry measurement can attain sensitivity as high as 100 nm±0.8 nm. Although suitable for some present needs, increased target sensitivity is desirable. Moreover, as feature sizes and critical dimensions continue to shrink lithographic processes are under continuing pressure. This will continue for the foreseeable future. Therefore, added sensitivity will continue to be a priority.

Therefore, although such existing processes and tools are suitable for their intended purposes, improvements can be made. The present invention seeks to go beyond the limitations and structural shortcomings of existing technologies.

SUMMARY OF THE INVENTION

In accordance with the principles of the present invention, an improved scatterometry target and methods for its design and use are disclosed.

In general, the present invention is directed toward target having a lattice of many periodically spaced and uniformly configured metrology features arranged in an array pattern over a target region. The lattice includes at least one defect region in the lattice, the defect region includes a defect feature that can be represented by the presence of one or more specific intentionally introduced defects. For example, a defect feature can comprise a missing metrology feature as well as the presence of an aberrant feature. Accordingly, the inventors point out that the defect region incorporates the presence or absence of at least one intentionally introduced defect feature. Thus, the defect region is configured to enable the target to demonstrate increased sensitivity to one or more selected parameters of interest. The invention further encompassing associated methods of implementing the target and evaluating the parameters of interest.

One embodiment of the invention comprises a scatterometry target comprising a photonic crystal lattice of a plurality of periodically spaced and uniformly configured metrology features arranged in an array pattern over a target region. The lattice includes at least one defect region in the photonic crystal lattice. The defect region includes at least one intentionally introduced defect feature. Said defect can be characterized by the presence or absence of an intentionally introduced defect feature. The defect comprising a localized deviation from the array pattern of the photonic crystal lattice. The defect enabling increased sensitivity of the target to one or more predetermined parameters of interest that can be associated with a characteristic of the defect.

In another embodiment the invention encompasses a method of generating a scatterometry target that is sensitive to at least one desired parameter of interest. In one implementation, the method includes operations of defining the parameter(s) of interest. Providing a library of archetypal target patterns suitable for generating target patterns effective for measuring the parameter(s) of interest. Defining a test range over which selected parameters can vary. Simulating the response of selected archetypes over a range of process conditions. Evaluating simulated response information to determine a target design suitable for implementation.

Other aspects and advantages of the invention will become apparent from the following detailed description and accompanying drawings which illustrate, by way of example, the principles of the invention.

BRIEF DESCRIPTION OF THE DRAWINGS

The following detailed description will be more readily understood in conjunction with the accompanying drawings, in which:

FIGS. 3(a)-3(h) are simplified diagrams illustrating various 2D embodiments of periodic targeting structures with intentionally introduced defects configured to enhance the sensitivity of the target to a selected parameter of interest in accordance with an embodiment of the invention.

It is to be understood that in the drawings like reference numerals designate like structural elements. Also, it is understood that the depictions in the Figures are not necessarily to scale.

DETAILED DESCRIPTION OF THE INVENTION

The present invention has been particularly shown and described with respect to certain embodiments and specific features thereof. The embodiments set forth hereinbelow are to be taken as illustrative rather than limiting. It should be readily apparent to those of ordinary skill in the art that various changes and modifications in form and detail may be made without departing from the spirit and scope of the invention.

In general, the present invention encompasses enhanced scatterometry targets enabling greater sensitivity to parameters of interest than existing technologies. Such targets as disclosed herein can enable increased accuracy and sensitivity and can enable a de-correlation of some parameters and reduce the effects of undesirable process variations.

Figure 1:
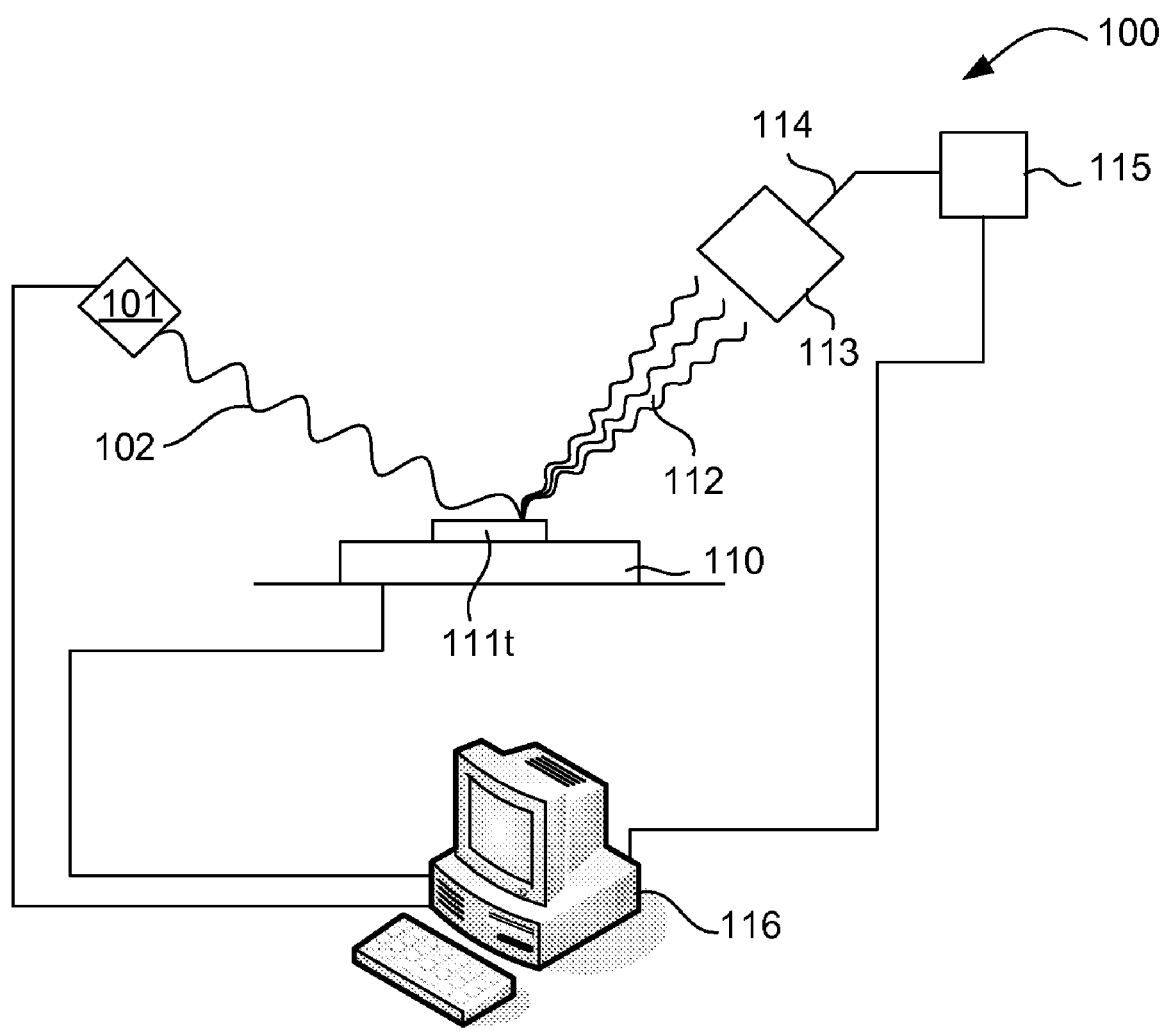
FIG. 1 illustrates a scatterometry device suitable for illuminating an inventive target in accordance with the principles of the invention.

FIG. 1 schematically depicts a very simplified embodiment of a portion of a scatterometry tool 100 used in conjunction with the targets disclosed herein. The inventors contemplate that such scatterometry tools include, but are not limited to spectroscopic ellipsometers, spectroreflectometers, polarized spectroreflectometers, angle resolved ellipsometers, angle resolved scatterometers, as well as other associated scatterometry tools. In the depicted embodiment, an illumination source 101 produces an illumination beam 102 that is directed onto a subject wafer 110 (or other substrate). More particularly, the illumination beam 102 is directed onto a scatterometry target 111t of the present invention. The beam 1102 impinging upon the target 111t is subject to scattering and diffraction. The scattered signal 112 is captured by a light detection apparatus 113 sensitive to various optical properties of the scattering signal 112 (e.g., variations in the polarization, extent of scatter, etc.). The light detection apparatus 113 converts the scattered signal 112 into an electrical signal 114 that is capable of being processed by a processor (e.g., a microprocessor, computer, or other suitably capable electronic device) 115 to obtain useful information concerning the patterns formed on the substrate. In particular, target information is obtained, such information can specifically relate to parameters of interest. An example, of such a scatterometry tool includes, but is not limited to a tool like the SpectraCD 100 produced by KLA-Tencor Corporation of San Jose, Calif.

The inventor points out that the entire depicted apparatus 100 can be controlled by a computer system 116. Such a computer system 116 can operate as a stand-alone computer system or part of the network. Additionally, the apparatus 100 of the present invention can operate on a distributed computer system having many computers. These computer systems can take many physical forms ranging from an integrated circuit, a printed circuit board, and a small handheld device up to a huge super computer. Additionally, computer systems are intended to apply to networked computer systems having many individual computers. Such networked systems can include local area networks (LAN's) or a wide area network (WAN's). An example of a LAN is a private network used by a mid-sized company with a building complex. Publicly accessible WAN's include, but are not limited to, the Internet, cellular telephone network, satellite systems and plain-old-telephone systems (POTS). Examples of private WAN's include those used by multi-national corporations for their internal information system needs. The network may also be a combination of private and/or public LANs and/or WANs. Such computer systems can be used to input data and otherwise control the scatterometry tool 100 implemented here.

In continuation, the inventor has taken advantage of certain recent discoveries in "photonic" crystallography and applied them to a metrology environment to produce a target and method capable of obtaining increased sensitivity.

In the prior art, scatterometry targets were configured with arrays of many uniformly sized features arranged in periodically spaced arrays. Much care was taken to generate targets having uniform size and shape as well as periodic spacing of great uniformity. Deviations from this uniformity were generally thought to degrade the quality, sensitivity, and accuracy of the information content obtained from such "defective" targets. For example, line edge roughness comprises a deviation from periodicity that degrade accuracy in CD measurements. These prior art target types have their uses but each suffers from limitations. The present invention provides an improved target that provides superior performance relative to known target types.

Research in the field of photonic crystals has revealed that the selective introduction of a "defect" into the photonic crystal lattice can cause strong resonances in an optical response that enables increased sensitivity to the presence of the defect. The inventors have applied this concept of increased resonance to a scatterometry target. As such, when an intentionally introduced defect is introduced into a uniform pattern of periodically arranged features (of a uniform configuration) of a scatterometry target, the target exhibits a surprising sensitivity to the deviations from periodicity of the "defect". The inventor has taken advantage of this surprise to generate target configurations that are believed to be even more sensitive to selected parameters of interest than the previously known target types.

Excellent background information on photonic crystals is widely available. One suitably wide survey of the basic information is contained in "Photonic Crystals" by J. Joannopoulos, R. Meade, & J. Winn. Many other associated works discuss and explain this topic. Also, particularly helpful are the photonic crystal tutorials by Prof S. Johnson at MIT which are available at http://ab-initio.mit.edu/photons/tutorial/ and helpful background is also found in the article entitled "Photonic Crystals: Periodic Surprises in Electro-Magnetism" found at http://ab-initio.mit.edu/photons/tutorial/L3-fab.pdf. The contents of each of these works are hereby incorporated by reference in their entirety for all purposes.

In regular crystallographic structures, such crystalline portions of semiconductor substrates, certain bands of "allowed" electronic energy states exist. Additionally, there are also bands of "non-allowed" electronic energy states. Photonic crystal research has shown that when periodic structures formed using lithography, nano-machining, or self assembly are made, they can demonstrate an analogous behavior defining "allowed" and "non-allowed" photonic energy states defining "photonic" band gaps. Photonic crystal research has also revealed that when a small minority of defects are introduced into the lattice of a periodic (e.g., crystallographic) structure, "allowed" states can be introduced within the photonic band gap that previously existed. The inventor has discovered that information of increased sensitivity can be obtained by introducing a "defect" into a periodic structure to introduce an "allowed" state into the photonic bandgap.

For example, in the prior art, a regular array of "holes" may be formed in a target to track and characterize the fidelity of hole formation processes used in a fabrication step. Such a target may be useful in tracking the accuracy of a via formation process used in forming contact vias in a layer of a wafer. Many other examples are immediately apparent to those of ordinary skill in the semiconductor processing arts. For example, a prior art target may include 10,000 holes having a diameter of 100 nm configured in a 100×100 array of holes having a periodic spacing of 400 nm. This example may have been applied to determine the accuracy of a process to the fabrication of 100 nm diameter holes in the wafer. The accuracy and sensitivity of such a target (sensitivity to, for example, variations in diameter) might be on the order of ±0.8 nm.

It has been discovered that increased sensitivity and accuracy can be obtained employing the principles of the invention. By creating a lattice of periodically spaced and uniformly configured metrology features and then intentionally introducing one or more defect metrology features the sensitivity of the target to one or more parameters of interest associated with the defect feature can be increased.

Figure 2A:
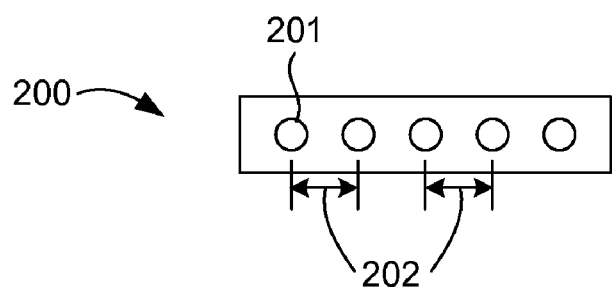
FIG. 2(a) is a simplified depiction of a periodic target of the prior art.

By lattice of periodically spaced and uniformly configured metrology features the inventor means a set of features having a uniform pitch across the target lattice and also having a uniform configuration. A uniform configuration means metrology features having a uniform shape and size across the target region. One such implementation is displayed in the extremely simplified example shown in FIG. 2(a) which depicts a target 200 having five regularly spaced holes 201 having a uniform pitch 202. In common usage in accordance with the principles of the invention, such a target would have many more such repeating units and extend into two dimensions by replicating the linear target with a fixed periodicity in an orthogonal direction.

Figure 2B:
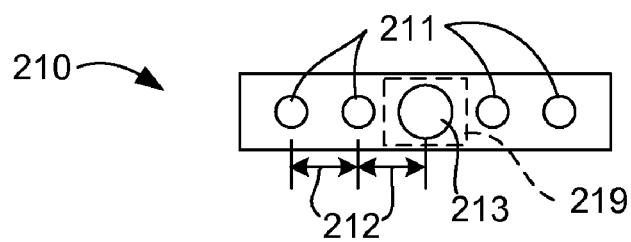
FIGS. 2(b)-2(d) are simplified diagrams illustrating aspects of periodic targeting structures of the present invention that incorporate intentionally introduced defects into the periodic array of the target to enhance the sensitivity of the target to a selected parameter of interest in accordance with an embodiment of the invention.

In one embodiment of the invention the inventor introduces a defect feature (See, FIG. 2(b)) into a defect region 219 of a target 210. Such defect features comprise intentionally introduced localized deviations from the periodic pattern. An attribute of these defect features is that they enable increased sensitivity of the target to at least one predetermined parameter of interest. The parameter(s) of interest being related to the nature and location of the defect. Such defect features can be an added feature or in some implementations, the absence of a feature.

In one extremely simplified example of such an inventive target, FIG. 2(b) depicts a target 210 having five regularly spaced holes having a uniform pitch. Such a target 200 is a one-dimensional (1D) target. However, in FIG. 2(b), the defect metrology feature 213 is enhanced by the presence of a larger "hole" in the pattern of regularly spaced (periodic) metrology features. In the depicted example, the pattern includes four smaller holes 211 having a periodic spacing 212 across the target 210. The defect metrology feature 213 is larger in diameter. Accordingly, the target will be more sensitive to measurements of the defect feature. For example, if the FIG. 2(a) features 201 are 100 nm then the sensitivity of the target is of a first level (e.g., on the order of ±0.8 nm). In a contrasting example, if the target of FIG. 2(b) has features 211 of 80 nm and the defect feature 213 has a diameter of 100 nm, then the target may have increased sensitivity to variations in diameter and may demonstrate increased accuracy and sensitivity to that parameter (diameter). For example, the target 210 may demonstrate an increased sensitivity to the diameter parameter of a second level (e.g., on the order of ±0.1 nm) superior to that of the first target 200. The increased sensitivity provide by the presence of the defect contradicts the previous teachings in the art which indicate that defects degrade the information obtainable from such targets.

Figure 2C:
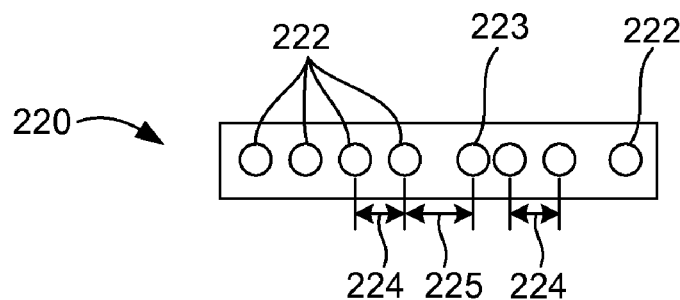

In another simplified 1D example, the inventor offers FIG. 2(c). The target 220 of FIG. 2(c) depicts a target 210 having a field of regularly spaced holes 222 having a uniform pitch and configuration (e.g., shape and size). The defect metrology feature 223 comprises an offset "hole" (of the same size) in the pattern of regularly spaced (periodic) metrology features. Accordingly, in this implementation, the target 220 may be more sensitive to measurements of spacing or displacement of the defect feature. For example, if the FIG. 2(c) features 222 are periodically spaced with a pitch 224 of 400 nm and the defect feature 223 has a first offset 225 of 700 nm with respect to one adjacent feature and perhaps a second offset of 100 nm with respect to another adjacent feature, then the target may have increased sensitivity to variations in offset and may demonstrate increased accuracy and sensitivity to that parameter (deviations from regular pitch).

Figure 2D:
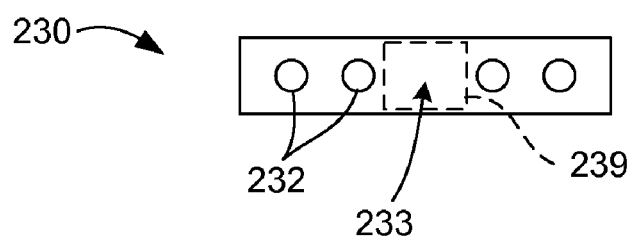

In another simplified 1D example, the inventor offers FIG. 2(d). The target 230 of FIG. 2(d) depicts a target having a field of regularly spaced holes 232 having a uniform pitch and configuration (e.g., shape and size). A defect region 239 includes a defect metrology feature 233 that comprises a missing "hole" in the pattern of regularly spaced (periodic) metrology features. Accordingly, in this implementation, the target 230 may be more sensitive to measurements of the edges of the adjacent features 232.

Thus, the defect metrology features in general represent a localized deviation from the regular periodic pattern (and or shape, size, and so on) of the target. The inventor points out that each lattice can include more than one defect feature. Such defects can comprise deviations in the form of different sized or shaped targets, as well as variations from the periodicity of the periodic array of which they form a part.

The inventor specifically contemplates targets comprising higher order target lattices including two-dimensional (2D) and three-dimensional (3D) lattices. In each case, the presence of the defect feature contemplates increased sensitivity of the target to a predetermined parameter of interest.

Figure 3A:
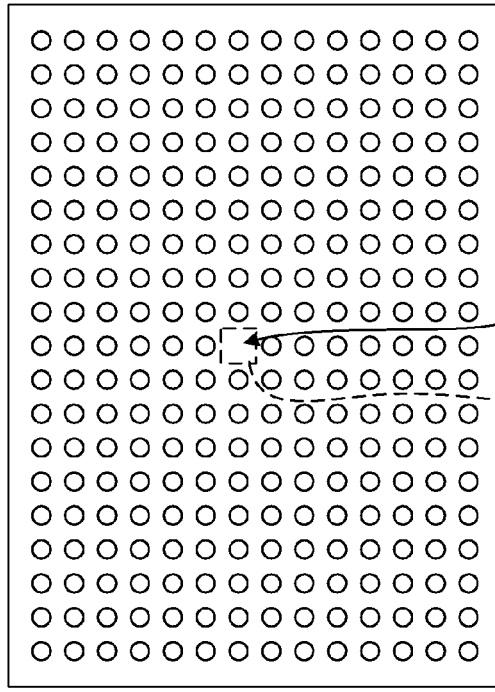

In another set of implementations the inventor makes reference to FIGS. 3(a)-3(h) which reference 2D scatterometry targets. FIG. 3(a) is a typical scatterometry target having a periodic set of consistently shaped and sized metrology features. In this example case, the metrology features comprise a set of circular holes arranged in a two dimensional periodic array of holes. The pitch of the holes (metrology features) of the array is the same for each metrology feature. This is one application of a target into which appropriate defect features can be introduced.

Figure 3B:
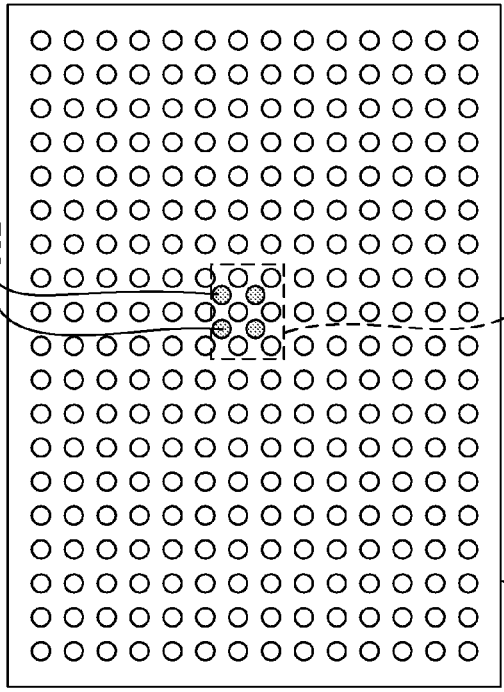
Figure 3C:
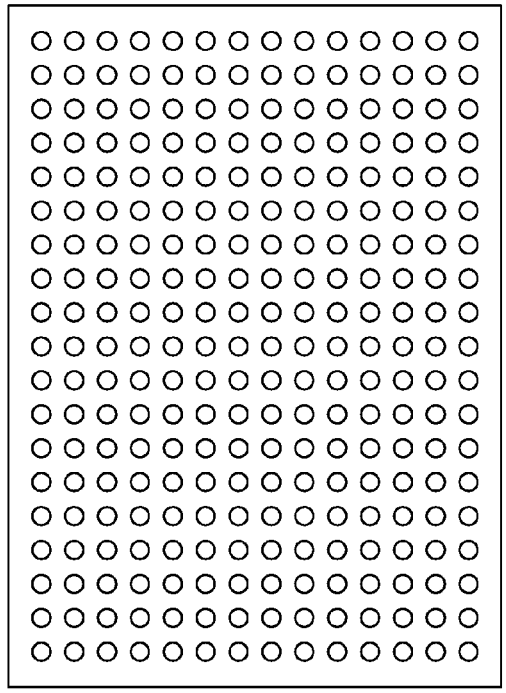
Figure 3D:
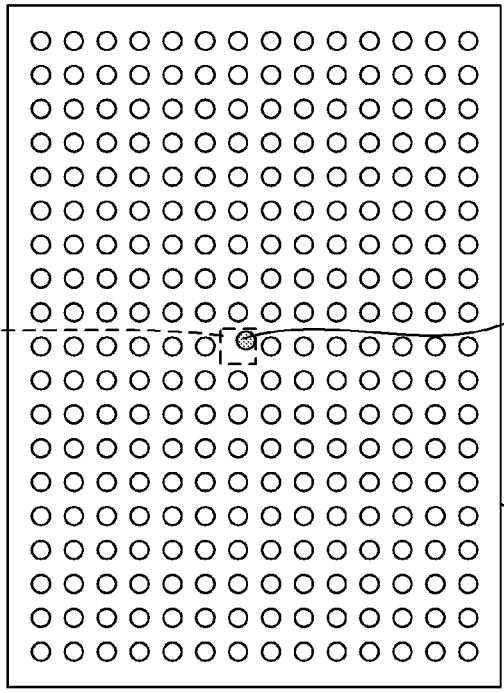

FIG. 3(b) is a simplified depiction of one embodiment of a 2D scatterometry target 310 constructed in accordance with the principles of the invention. As before, the target includes a periodic set of consistently shaped and sized metrology features. In this example case, the metrology features comprise a set of circular holes arranged in a two dimensional periodic array of holes. The pitch of the metrology features of the array is the same for each metrology feature. Additionally, a defect region 311 is defined in the target. This defect region can be located anywhere within the target, but in this embodiment the defect region is in the target center. Within the defect region 311 is a defect metrology feature 312. In this depiction, the defect metrology feature is simply the absence of any feature at all. The inventor points out that various target embodiments can include many defect metrology features on each target rather than just one. Additionally, the defect region itself can comprise many defect regions scattered over the target (or concentrated in a selected portion of the target).

FIG. 3(*c*) is another simplified embodiment of a 2D scatterometry target 220 constructed in accordance with the principles of the invention. As before, the target includes a periodic set of consistently shaped and sized metrology features. Again, in this example, the metrology features comprise a set of circular holes arranged in a two dimensional periodic array of holes. The pitch of the metrology features of the array is the same for each metrology feature. The features are of course periodically spaced in the "x" and "y" coordinate axes to enable 2D periodicity. Additionally, a defect region 321 is defined in the target. As before and as with most embodiments, the defect region can be located anywhere within the target. Here, the defect region is in the target center. Within the defect region 321 is a defect metrology feature 322 (the darkened feature). In this depiction, the defect metrology feature is an offset hole of the same size and shape as the regular periodic features. The offset is a non-periodic distance (in one or both axes) with respect to the periodic array. This embodiment will have increased sensitivity to the displacement measurements associated with the defect feature 322. The defect feature can be positioned to enable increased sensitivity to displacement along one or more displacement axes (in the depicted target the sensitivity could, for example, be sensitive to displacement along both an "x" axis and a "y" axis). Additionally, as before, various target embodiments can include more than one defect metrology feature on each target. Moreover, the defect region itself can comprise many defect regions scattered over the target (or concentrated in a selected portion of the target).

FIG. 3(*d*) depicts another simplified embodiment of a 2D scatterometry target 330 constructed in accordance with the principles of the invention. As before, the target includes a periodic set of consistently shaped and sized metrology features. Again, in this example, the metrology features comprise a set of circular holes arranged in a two dimensional periodic array of holes. The pitch of the metrology features are of course periodically spaced in the "x" and "y" coordinate axes to enable 2D periodicity. Additionally, a defect region 331 is defined in the target. As before and as with most embodiments, the defect region can be located anywhere within the target. Here, the defect region 331 is in the target center. Within the defect region 331 are a multiplicity of defect metrology features 332 (the darkened features). In this depiction, the defect metrology features are a multiplicity of inserted holes that comprise an insertion defects. This embodiment can demonstrate increased sensitivity to, for example, the diameter of defect features or the location of defect features relative to the lattice. Although the depicted defects are concentrated in a central defect region, as mentioned before, various target embodiments can include a plurality of such defects placed at many locations throughout the target.

FIG. 3(*e*) depicts another simplified embodiment of a 2D scatterometry target 340 constructed in accordance with the principles of the invention. As before, the target includes a periodic set of consistently shaped and sized metrology features, here, comprising a set of circular holes arranged in a two dimensional periodic array. The pitch of the metrology features are of course periodically spaced in the "x" and "y" coordinate axes to enable 2D periodicity. Additionally, a defect region 341 is defined in the target. As before and as with most embodiments, the defect region can be located anywhere within the target. Here, the defect region 341 is in the target center. Within this defect region 341 is a defect metrology features 342 (the darkened feature) comprising a hole of increased size relative to the array of holes. Such an embodiment can have increased sensitivity to the increased size of the hole. Additionally, a defect metrology feature comprising a hole smaller than array holes can provide a target having increased sensitivity to the smaller sized hole. In one example, such a target could be used as follows. A process used to form 100 nm diameter holes is to be performed and monitored using a target. In one embodiment, a target is formed including an array of periodic holes that are 120 nm in diameter. A suitable defect metrology feature could be a 100 nm hole. The resulting target could have an increased sensitivity relative to 100 nm holes. Accordingly, such a target could provide a highly sensitive mechanism for monitoring the formation of 100 nm diameter holes. As mentioned previously, the defect features depicted are concentrated in a central defect region. However, as mentioned before, various target embodiments can include a plurality of such defects placed at many locations throughout the target.

FIG. 3(*f*) depicts another simplified embodiment of a 2D scatterometry target 350 constructed in accordance with the principles of the invention. As before, the target includes a periodic set of consistently shaped and sized metrology features, here, comprising a set of circular holes arranged in a two dimensional periodic array. The pitch of the metrology features are of course periodically spaced in the "x" and "y" coordinate axes to enable 2D periodicity. Additionally, a defect region 351 located within the target and includes therein a defect metrology feature 352 (the darkened elliptical feature) comprising a hole of a different shape (here, an elliptical hole) relative to the array of (which in this case are intended to be circularly configured holes). Such an embodiment can have increased sensitivity to the ellipticity of the hole. Additionally, different shapes of the defect metrology feature 252 will demonstrate increased sensitivity to the shape of the defect feature, (e.g., square, rectangles, conical sections, and so on). In general, such embodiments can be very sensitive to variations in shape. As mentioned previously, the defect features can include a plurality of such defects placed at many locations throughout the target.

FIG. 3(*g*) depicts a target with a line deletion defect 361 that may be useful for measuring a variety of parameters. An example of such a feature includes, but is not limited to a line defect. Also, such targets can be made sensitive to variations in "hole" size and shape as well as other parameters. Also, FIG. 3(*h*) is a target with an "extended defect" 371 comprising defect features having a greater pitch (in at least one axis) enabling greater sensitivity to selected parameters of interest. In some examples, such a target design may be sensitive to the relative size of the metrology features or sensitive to the size of the defect 371 or sensitive to the difference in size between the defect and the ordinary periodic metrology features.

Figure 4:
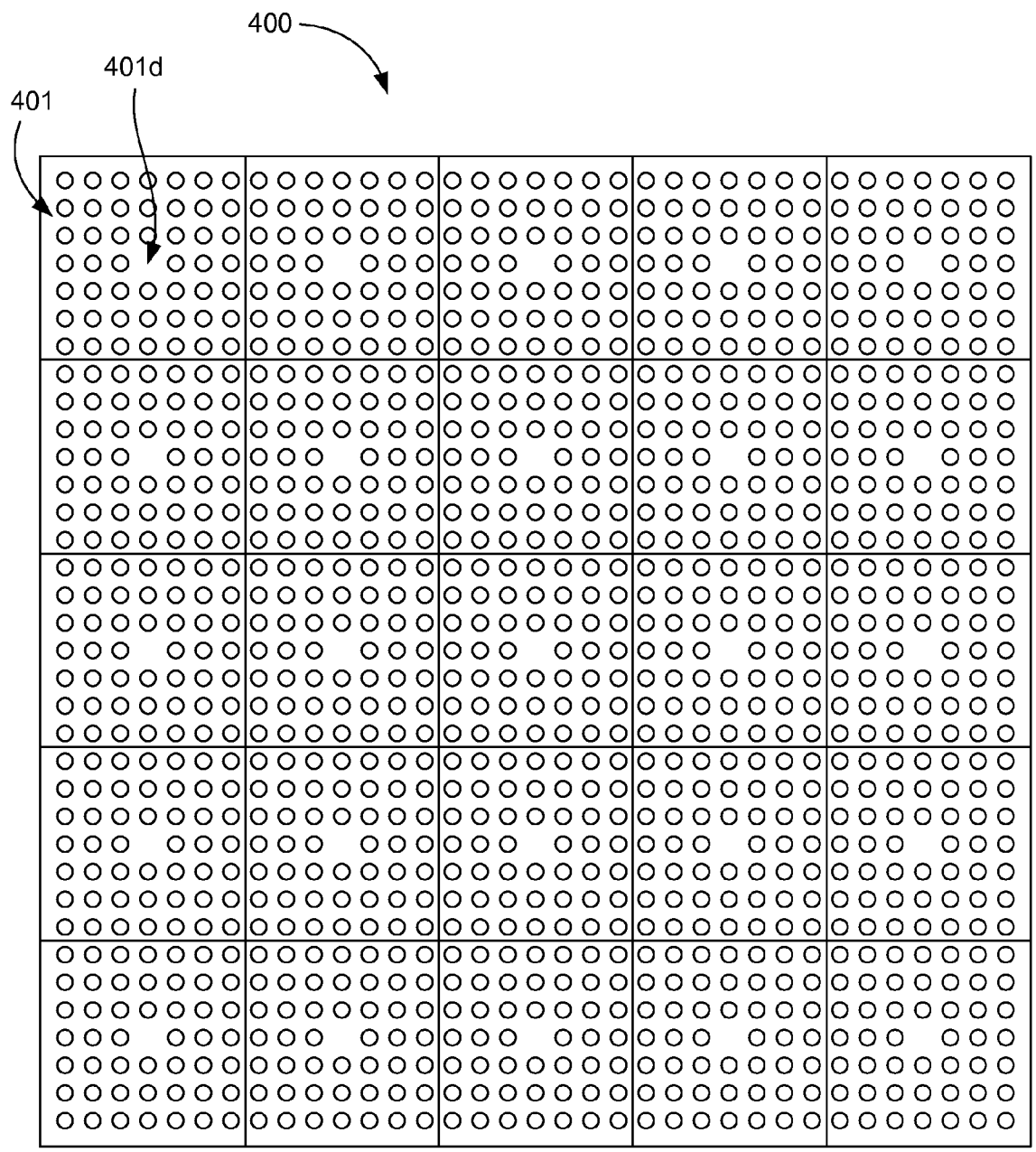
FIG. 4 is a simplified plan view of a periodic target configured as an array of repeating sub-arrays of periodic targets each with an intentionally introduced defect configured to enhance the sensitivity of the target to a selected parameter of interest in accordance with an embodiment of the invention.
Figure 5A:
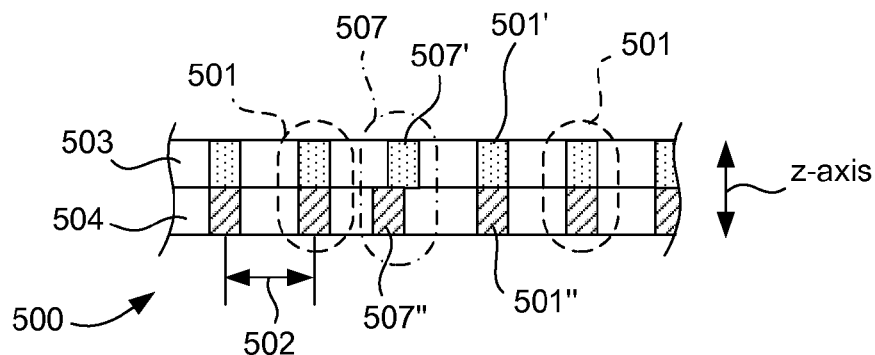
FIGS. 5(a) & 5(b) are simplified cross-section views illustrating various 3D embodiments of periodic targeting structures with intentionally introduced defects configured to enhance the sensitivity of the target to a selected parameter of interest in accordance with an embodiment of the invention.
Figure 5B:
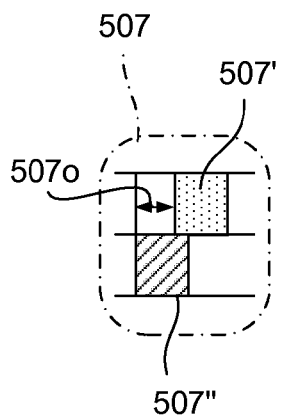
Figure 5C:
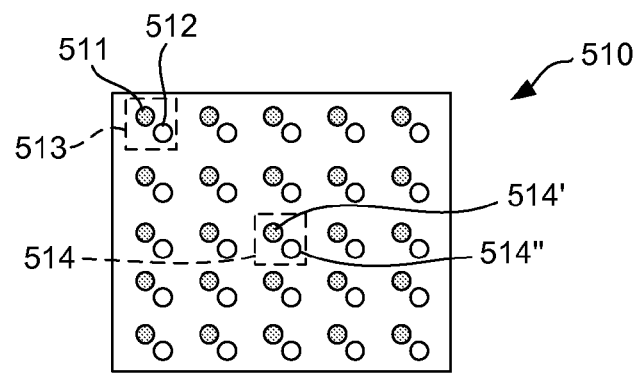
FIG. 5(c) is a simplified plan view illustrating one 3D target embodiment with an intentionally introduced defect in a periodic array of features configured to enhance the sensitivity of the target to a parameter of interest in accordance with an embodiment of the invention.
Figure 5D:
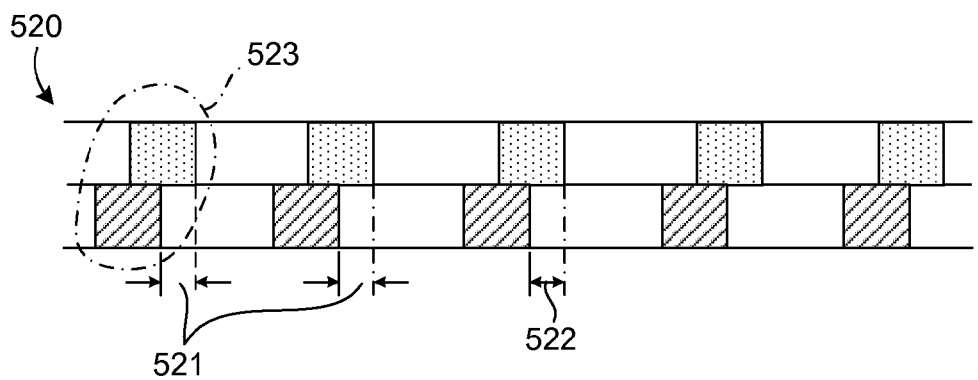
FIG. 5(d) is another simplified cross-section view illustrating a 3D embodiment with an intentionally introduced defect configured to enhance the sensitivity of the target to a selected parameter of interest in accordance with an embodiment of the invention.

Additionally, 2D array targets can be used in repeating configurations of unit cells in selected embodiments. Many parameters of interest can be interrogated in this manner. One particularly useful implementation of such an embodiment is in a scatterometry overlay (SCOL) target. For example, FIG. 4 depicts one example of such a multi-cell target. In this depicted example, the target 400 includes an array of 25 lattice unit cells. Each cell 401 is configured identically to each other cell in the target lattice. The inventor points out that any cell configuration can be used to form the unit cells, including, but not limited to, any of the configurations discussed in this patent. In the depicted example, the each cell 401 includes an identical defect metrology feature 401*d* (here, a missing metrology feature). The orientation and position of the defect metrology feature 401*d* is the same for each unit cell 401. Thus, such multi-cell target lattices for a repeating pattern of cells to generate a target. Such structures can in some circumstances provide increased sensitivity to a parameter of interest. In some implementations, the cells are smaller than the spot size but can also be the same approximates size as the spot size or larger than the spot size if desired.

Additionally, three-dimensional (3D) array targets can be used in selected embodiments. Many parameters of interest can be interrogated in this manner. One particularly useful implementation of such an embodiment is in a scatterometry overlay (SCOL) target.

FIGS. 5(*a*)-5(*d*) are simplified side cross-section views of simplified example 3D targets. In one extremely simplified example of such an inventive target, FIG. 5(*a*) depicts a portion of a 3D target 500 suitable for detecting overlay defects. Such a target, in addition to having a 1D or 2D arrangement on a target surface also includes a z-axis (depicted) which can enable further targeting information. For example, a variation of the features in the z-axis direction can be used to obtain information concerning selected parameters of interest. In the depicted embodiment, the target 500 includes a plurality of periodic metrology features 501 (examples of such features being within the dashed-lines). These features are contained in at least two layers (e.g., the depicted first layer 503 and second layer 504). The plurality of periodic metrology features 501 can be arranged having constant pitch 502 between the periodic metrology features 501. The inventors point out that in this implementation, each periodic metrology feature 501 includes an upper portion 501' and a lower portion 501". These portions can be defined as holes, plugs of different materials that can be different still from the surrounding materials and layers, such portions can in any case be any other discernable distinct features. In this embodiment, an upper portion 501' is aligned with a complementary lower portion 501" to form each periodic metrology feature 501. Alternatively, the target can be defined by a periodic array of features constructed so that each upper portion 501' has a constant offset with respect to an associated lower portion 501".

Additionally, the target 500 includes a defect metrology feature 507 (encircled by the alternating dot/dashed lines) that includes an offset between its upper portion 507' and its lower portion 507". With reference to FIG. 5(*b*) the inventor points out that the offset 507*o* between the upper portion 507' and a lower portion 507" enables a target to have increased sensitivity to the offset as compared to targets where all features demonstrated the offset. As mentioned before, targets having more than one defect metrology feature can be used. The offset can be in two dimensions. Using the depicted embodiment as an example, one offset can be in the left to right direction with another offset being arranged in and out of the page. Such targets will enable measurements of offsets in two directions using the same target enabling a more compact target capable of delivering more information.

Additionally, many different embodiments can be constructed designed to interrogate different parameters of interest. For example, the regularly spaced (periodic) metrology features can comprise a feature having the upper portion and its associated lower portion with a defined and uniform offset and the defect feature configured so that its upper portion and its associated lower portion are aligned with no offset. Or the defect can be offset in one axis but not another. Alternatively, the defect feature can be the absence of any features. The inventor points out that these examples are merely intended to illustrate some aspects of the invention rather than to place any limits upon it. Many different defect arrangements and target configurations are contemplated by the inventor and specifically the inventor contemplates that many configurations not specifically identified in this patent are suitable for enhancing measurements of various parameters of interest in accordance with the principles of the invention.

FIG. 5(*c*) is a simplified plan view of an example 3D target embodiment. The depicted 3D target 510 can be used to detect various defects and can be used to provide a target with increased sensitivity to overlay defects. Such a target, in addition to having a 1D or 2D arrangement on the target surface, further includes a depth (z-axis) dimension. For example, target 510 includes at least two layers and feature portions formed on more than one layer for each metrology feature. As such, portions of each metrology feature 513 include a first portion (the dark dots 511) formed on a first layer and a second portion (the light dots 512) formed on a second layer. The target 510 again includes a plurality of periodic metrology features (e.g., 513) arranged with a regular pitch and spacing across the target. In this implementation, an example feature 513 includes a lower second portion 512 that is offset with respect to the upper first portion 511. In this embodiment, portions 511, 512 are offset holes (in this case offset in both the x and y axes) in a specified arrangement configured to generate the periodic metrology feature 513. As described previously, the portions can be holes, plugs of different materials, or any other discernable distinct features. The periodic features are arranged at regularly spaced intervals to form a target array or photonic lattice. Additionally, the target 510 includes a defect region 514 containing a defect feature. In this embodiment, the defect feature formed in the region 514 also includes a defect upper portion 514' arranged in a defect configuration with a complementary lower portion 514" to form the defect metrology feature. As can be seen in the illustration, the defect feature is configured to include an offset relative to the periodic metrology features 513. In the depicted embodiment, the offset is along both the x and y axes. This has the advantage of enabling measurement of both x and y offset using the same target feature. However, the inventor points out that, in other examples and implementations the offset can be in only one axis if desired. In another approach, the defect region 514 can be absent of any features altogether creating a different kind of "defect". In another approach, the defect region 514 can be larger encompassing many defect metrology features. Or as explained previously, there can be several defect regions 514 containing many defect features. Thus, in general such 3D targets can enable measurements of periodic spacing or displacement in a length direction, in a width direction, and in a depth direction as well as other measurements.

In one example of another novel inventive approach, the target can be defined by a periodic array of features constructed so that each upper portion 501' has a constant offset with respect to an associated lower portion 501".

FIG. 5(*d*) illustrates a multi-layer target 520 having a set of periodic features 523 similar to that of FIG. 5(*a*). However, in the FIG. 5(*d*) implementation, the periodic features 523 each have a first offset 522. The periodic features 523 are arranged in a periodically spaced apart configuration. Also, a defect metrology feature 524 is included in the target 520. The defect metrology feature 524 is configured to include a second offset 522 that is different from the first offset 521. Such targets can be useful as having increased sensitivity to the second offset distance 522 or the difference between the first and second distances.

Such targets can include as few as five metrology features and at least one defect metrology feature. However, targets of a much larger size are generally used. In general, the targets are usually a bit larger than the spot size produced by the inspection tool used to inspect the target. Thus, it an inspection beam has a spot size in the range of about 20-50 micrometers (μm), the targets are generally at least that big. In one example, a target can be about 40 μm×40 μm in size having an array of metrology features of 100×100 features to generate and array of about 10,000 metrology features. As few as one defect feature can be present and as many as thousands of defects can be present, depending on parameter of interest and the nature of the defect feature as well as the lattice and cell configuration. The inventor specifically notes that the foregoing is an example only and is not intended to limit the scope of the invention. Moreover, as well indicated above, many other target configurations are, of course, possible.

The inventor points out that the nature of the invention renders the utility of each target design somewhat unpredictable. Therefore, in order to determine whether a given target design is suitable for accurate and precise measurement of a parameter of interest certain simulations are typically performed to determine target suitability for a given purpose. Example simulation software suitable for such implementations include, but are not limited to, MEEP which is a free finite-difference time-domain (FDTD) simulation software package developed at MIT to model electromagnetic systems. MEEP is freely accessible at http://ab-initio.mit.edu/meep/ and is hereby incorporated by reference. Also, suitable is the MIT Photonic-Bands (MPB) package. MPB is a program for computing band structures (dispersion relations) of optical systems. MPB was developed by Steven G. Johnson of the Joannopoulos Ab Initio Physics Group in the Condensed Matter Theory division of the MIT Physics Department. MPB is accessible at http://web.mit.edu/meep_v0.10/mpb/doc/index.html and is also hereby incorporated by reference. The inventor also points out that software for implementing rigorous couple wave approximation's (RCWA) and other finite-difference time-domain (FDTD) simulation software packages can also be employed in this capacity.

Figure 6:
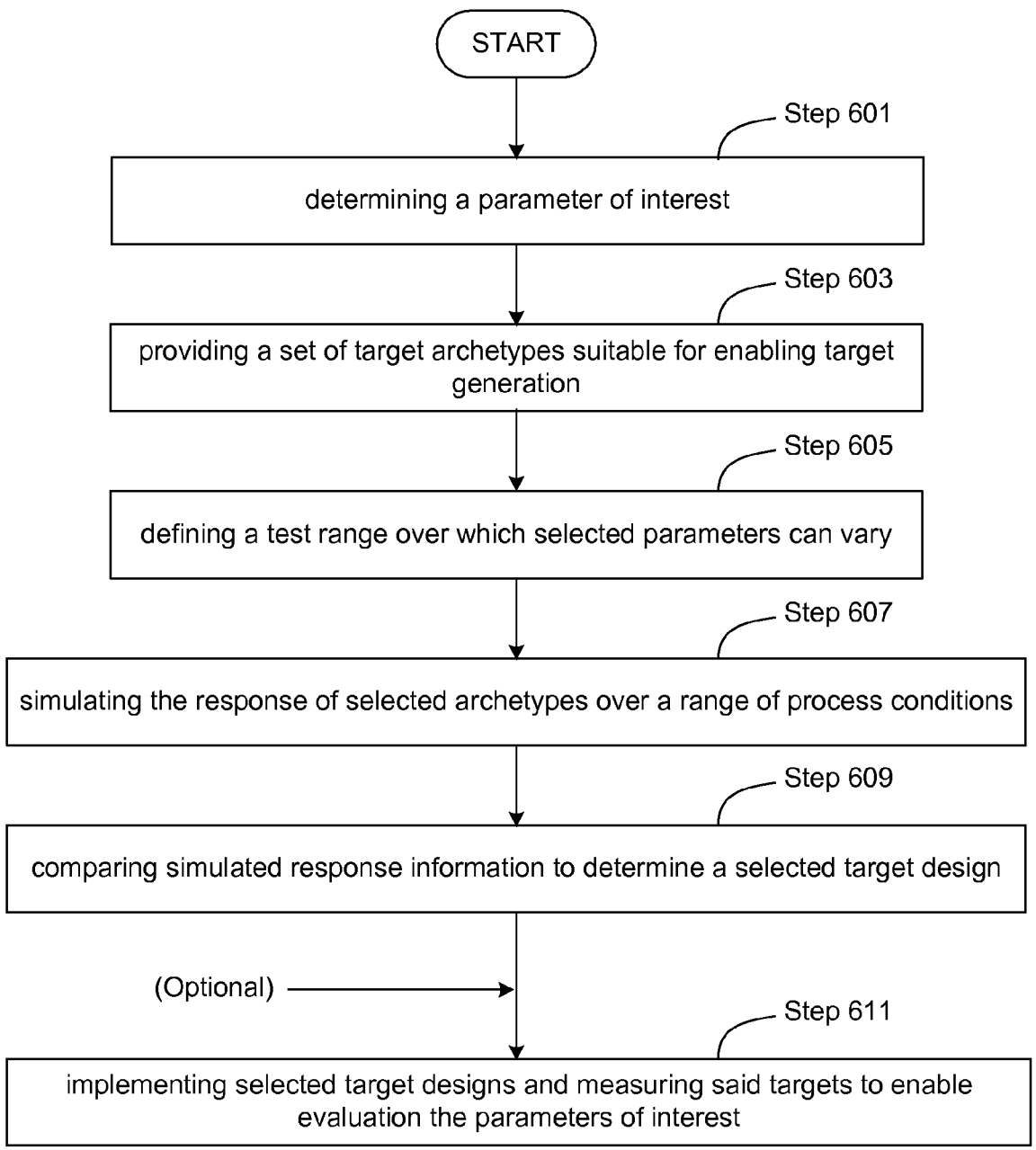
FIG. 6 is a simplified flow diagram describing some aspects of a method implementation and/or a computer readable instruction set operable with a computer and computer readable media in accordance with the principles of the invention.

The invention also comprises many implementation approaches. In FIG. 6 a method for determining suitable targets is disclosed. First, one or more parameters of interest are determined (Step 601). Such parameters can refer to feature configuration (including but not limited to feature size, shape, presence or absence, and so on), feature displacement (including displacement on one layer (or many layers e.g., overlay measurements and the like)), angle of a feature, undercut characteristics, material properties such as refractive index or strain, or other many, many, other parameters of interest. Such parameters are well known to those having ordinary skill in the art.

A set of target archetypes are provided to enable a basis for target generation (Step 603). Such archetypes represent various types and numbers of defects introduced into various configurations of otherwise periodic structures. Moreover, other archetypes can be generated as needed. Typical of such archetypes are defect cells and lattices having an offset defect metrology feature which is well suited to measure overlay displacement. The size and shape archetypes have also been briefly touched upon.

Once a set of suitable archetypes has been generated (said parameters being useful for providing measurable information concerning the desired parameter or parameters of interest) a range of expected variations in various process parameters and outcomes is accommodated. The range of parametric variation (variance of various process parameters, including but not limited to the process window) for the modeled process is defined (Step 605). This range is intended to accommodate expected process variations and expected error determinants associated with the manufacturing process window. In short, the variations in process window are included in the modeling process used to generate the target. Examples of important parameters used in determining a useful process window include, but are not limited to, the process parameters of the inspection tools used, the variations of size, shape, displacement, and so on encountered in an average process used to form the layers being inspected, the various materials properties for the materials used and so on. In one typical example, the know variations in inspection tools are taken into consideration and the expected error in the manufacturing process over the range of fabrication conditions is considered as well as the properties of the materials at issue. For example, if a process is known to produce features ranging from 100 nm to 300 nm under ordinary process conditions (or more likely from about 80 to 100 nm), this property is taken into consideration in defining the range of expected variation for the modeled system.

Then, once the archetypes are selected and the breadth of the various process variations are determined, the response of each of the selected archetypes is simulated over the various conditions in the process window (Step 607). This can be done using certain selected simulations software programs. As explained above, one example of a suitable software approach is the MPB software package (available for example at http//:ab-initio.mit.edu/wiki/index.php/MIT-_Photonic_Bands and elsewhere) as well as other simulations software. A number of simulations are run across the range of expected variation in the process window to obtain a set of simulated response information concerning each archetype or prospective target. For example, each archetype can be used to generate a series of simulated spectra across the range of parametric values. This simulated response information can be evaluated to determine the suitability of each target for a desired use.

Then, the set of simulated response information for all targets evaluated is compared to determine a most suitable target design selected from among the evaluated target designs (Step 609). Commonly, the various simulated response information are compared to obtain a target that gives the "best" response for measurement one or more parameters of interest. Typical factors one might consider include, but are not limited to, targets that produce large measurable changes in received signal when only small changes in the parameters of interest are occurring. This can result in a highly sensitive target. Also, targets that demonstrate decoupled behavior relative to other parameters. This means that targets that lack coupling to other parameters (when measurements are taken) are desirable. For example, if the parameter of interest was feature "size" of a feature formed on an underlying layer, a desirable target can be a target that is sensitive to feature size, but is relatively insensitive to variations in thickness of the underlying layer. Additionally, in many implementations, it is desirable that changes in a measured signal due to a change in a first parameter be distinguishable from changes in the measured signal due to variations in another (second) parameter. It is particularly useful that changes in measured signal due to variation in the first parameter be distinguishable from changes in the measured signal due to variation in the second parameter, even when the change in response due to the second parameter is large. Another measure of target suitability can be that the target produces a strong measurable signal in a range that the measurement tool is sensitive to. For example, the signal produced by the illuminated target is in a range where the measurement tool has a particularly high signal-to-noise ratio. Many other characterizations of a "good" or "best" target are, of course, readily apparent to one of ordinary skill and the foregoing list is intended as illustrative rather than limiting. The idea being that a suitable target is selected from the many possible archetypes.

In addition to evaluating archetypal target patterns over a range of parameter values as described above, the inventors contemplate that it may also be useful to use an algorithm, such as a genetic algorithm, to modify the target designs being evaluated. These modified target designs can then also be evaluated for their suitability to obtaining measurements of the parameter or parameters of interest. The implementation of such genetic algorithms is known. For example, information on such genetic algorithms can be found at http://en.wikipedia.org/wiki/Genetic_algorithm or in such publications as *Genetic Algorithms in Search, Optimization and Machine Learning* by David E. Goldberg (Addison-Wesley Professional, Jan. 1, 1989) or *An Introduction to Genetic Algorithms for Scientists and Engineers* by David A. Coley (World Scientific Publishing Company; November 1997).

Once targets are selected they can be implemented into the design formed on the semiconductor surface. Accordingly, such targets are formed in the desired portions of the surface, and are measured at appropriate times to obtain the desired information concerning the parameters of interest (Step 611).

Alternatively, the inventors contemplate that one or more target characterstics (e.g., target pitch, defect size or offset) can be varied and an optimization algorithm applied to determine selected values (for example selected optimal values for the characteristics) for the measuring of the parameters of interest. It will be appreciated that the target characteristics may or may not be the same as the parameters of interest for measurement. Well known optimization algorithms can include, but are not limited to the Levenberg-Marquardt algorithm, the steepest descent algorithm, the conjugate gradient method and the Nelder-Mead simplex algorithm. Further information on these and other related algorithms can be found in *Numerical Recipes, Third Edition: The Art of Scientific Computing* by Press, Teulkosky, Vetterling and Flannery (Cambridge University Press, Sep. 1, 2007.)

The invention also comprises target measurement approaches. Once the desired target type is determined and a wafer is fabricated having the desired target formed thereon, the wafer can be evaluated using appropriate measurement of the targets. The target(s) is "optimized" to enable measurement of one or more parameters of interest. A scatterometry measurement tool (spectroscopic ellipsometers, spectroreflectometers, polarized spectroreflectometers, angle resolved ellipsometers, angle resolved scatterometers, as well as other associated scatterometry tools) evaluates the target. Typically, this involves a measurement tool illuminating the target with an illumination beam to generate a collection beam. The collection beam is collected and analyzed to determine interrogate the parameters of interest. This information can then be used to determine the course of further process operations. For example, the information can be used to determine whether the wafer should be reworked, whether a process parameter from a prior step should be adjusted, whether process parameters later in the process should be adjusted to compensate for deviations from the ideal, and so on.

The invention disclosed here demonstrates many improvements over the state of the art and satisfies many of the needs in the industry as expressed in the foregoing paragraphs. Additionally, the present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors that many different metrology feature and defect feature arrangements and configurations can be established for targets constructed in accordance with the principles of the invention. Although only a few configurations are expressly disclosed herein, it should be appreciated by anyone having ordinary skill in the art that, using the teachings disclosed herein, many different configurations can be implemented and still fall within the scope of the claims. Further, reference in the claims to an element in the singular is not intended to mean "one and only one" unless explicitly stated, but rather, "one or more". Furthermore, the embodiments illustratively disclosed herein can be practiced without any element that is not specifically disclosed herein.

I claim:

1. A scatterometry target comprising:
   a photonic crystal lattice comprising a plurality of periodically spaced and uniformly configured metrology features arranged in an array pattern over a target region to be examined during a scatterometry measurement; and
   a defect region in the lattice, the defect region including at least one intentionally introduced defect feature comprising a localized deviation from the array pattern of the photonic crystal lattice.

2. The scatterometry target recited in claim 1,
   wherein the array pattern comprises a one-dimensional array of said metrology features.

3. The scatterometry target recited in claim 2,
   wherein the one-dimensional array comprises a line of periodically spaced apart metrology features having a common pitch between the metrology features.

4. The scatterometry target recited in claim 3,
   wherein the defect feature comprises a metrology feature having arranged in the one-dimensional array having a separation distance between an adjacent feature that varies from said common pitch between the metrology features.

5. The scatterometry target recited in claim 1,
   wherein the array pattern comprises a two-dimensional array of said metrology features.

6. The scatterometry target recited in claim 5,
   wherein the two-dimensional array comprises a grid array comprising a plurality of periodically spaced line structures.

7. The scatterometry target recited in claim 5,
   wherein the two-dimensional array comprises a plurality of periodically spaced apart features arranged with a periodic spacing in a length direction and in a width direction.

8. The scatterometry target recited in claim 5,
   wherein said periodic spacing is the same for the length direction and the width direction.

9. The scatterometry target recited in claim 5,
wherein the two-dimensional array comprises a plurality of periodically spaced features arranged having a first periodic spacing in a length direction and a second periodic spacing in a width direction.

10. The scatterometry target recited in claim 5,
wherein the array pattern is configured in at least one of a hexagonal, rhomboid, or non-rectangular shape.

11. The scatterometry target recited in claim 1,
wherein the array pattern comprises a three-dimensional array of said metrology features.

12. The scatterometry target recited in claim 1,
wherein the defect feature comprises the absence of at least one of the periodically spaced and uniformly configured metrology features in the defect region in the lattice.

13. The scatterometry target recited in claim 1,
wherein the plurality of periodically spaced and uniformly configured metrology features are of a first size, and
wherein the at least one intentionally introduced defect feature is of a second size, and the first and second sizes are different size from each other.

14. The scatterometry target recited in claim 1,
wherein the plurality of periodically spaced and uniformly configured metrology features are of a first size, the at least one intentionally introduced defect feature is of a second size, and
wherein the first and second sizes are different size from each other, thereby increasing the sensitivity of the target to one or more parameters of interest.

15. The scatterometry target recited in claim 1,
wherein each of the plurality of periodically spaced and uniformly configured metrology features of the lattice are spaced apart at a consistent uniform first distance from one another,
wherein the at least one intentionally introduced defect feature is spaced apart from the periodically spaced and uniformly configured metrology features at a second distance that is not the same as said first distance, and
wherein the first and second distance are different.

16. The scatterometry target recited in claim 1,
wherein the lattice of the periodically spaced and uniformly configured metrology features comprises metrology features of a first shape, and
wherein the at least one intentionally introduced defect feature is of a second shape, and the first and second shapes are different from each other.

17. The scatterometry target recited in claim 1, wherein the target region includes several of said photonic crystal lattices configured so that each photonic crystal lattice is identical to each other photonic crystal lattice of the target.

18. A scatterometry target comprising,
a lattice comprising a plurality of periodically spaced and uniformly configured metrology features arranged in an array pattern over a target region; and
a defect region in the lattice, the defect region including at least one intentionally introduced defect feature, the presence of the defect feature enabling increased sensitivity of the target to one or more predetermined parameters of interest,
wherein the plurality of periodically spaced and uniformly configured metrology features include multilayer features formed on at least two different layers of the target and wherein a portion of the feature formed on a first target layer is one of offset or aligned with respect to a portion of the feature formed on a second target layer to define a first offset distance,
wherein the at least one intentionally introduced defect feature is a multilayer feature formed on said at least two different layers of the target and wherein a portion of the defect feature is formed on the first target layer so as to be one of offset or aligned with respect to a portion of the defect feature formed on the second target layer to define a second offset distance, and
wherein the first and second offset distances being different from one another.

\* \* \* \* \*